US00PP29221P2

(12) United States Plant Patent
Takahashi

(10) Patent No.: US PP29,221 P2
(45) Date of Patent: Apr. 10, 2018

(54) ***HYDRANGEA* PLANT NAMED 'YHLAX15'**

(50) Latin Name: *Hydrangea macrophylla*
Varietal Denomination: YHLAX15

(71) Applicant: Taiei Kaen Nursery Ltd., Narita (JP)

(72) Inventor: Yasuhiro Takahashi, Narita (JP)

(73) Assignee: Taiei Kaen Nursery, Ltd., Narita (JP)

( * ) Notice: Subject to any disclaimer, the term of this patent is extended or adjusted under 35 U.S.C. 154(b) by 0 days.

(21) Appl. No.: 15/530,651

(22) Filed: Feb. 15, 2017

(51) Int. Cl.
*A01H 5/02* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — Audrey Charles

(57) ABSTRACT

A new and distinct cultivar of *Hydrangea* plant named 'YHLAX15', characterized by its light pink-colored inflorescences under alkaline growing condition, light violet-blue colored inflorescences under acidic growing conditions, medium green-colored foliage, and moderately vigorous, upright growth habit, is disclosed.

1 Drawing Sheet

Latin name of genus and species of plant claimed: *Hydrangea macrophylla.*

Variety denomination: 'YHLAX15'.

BACKGROUND OF THE INVENTION

The present invention relates to a new and distinct cultivar of *Hydrangea* plant botanically known as *Hydrangea macrophylla* and hereinafter referred to by the cultivar name 'YHLAX15'.

The new cultivar originated in a controlled breeding program in Narita, Japan during June 2008. The objective of the breeding program was the development of *Hydrangea* cultivars that have violet-blue colored inflorescences under acidic growing conditions and have single-type florets with wavy sepal margins.

The new *Hydrangea* cultivar is the result of cross-pollination. The female (seed) parent of the new cultivar is a proprietary *Hydrangea macrophylla* breeding selection coded TKH2000, not patented, characterized by its single-type, mophead, non-wavy margin sepals, light pink-colored inflorescences (light violet-blue colored under acidic growing conditions), medium green-colored foliage, and moderately vigorous, upright growth habit. The male (pollen) parent of the new cultivar is 'Kiyosumi sawa', not patented, characterized by its single-type, lacecap, non-wavy margin sepals, medium red-picotee colored inflorescences, deep green foliage with burgundy flushes, and vigorous, upright growth habit. The new cultivar was discovered and selected as a single flowering plant within the progeny of the above stated cross-pollination during June 2011 in a controlled environment in in Narita, Japan.

Asexual reproduction of the new cultivar by softwood cuttings since June 2011 in Narita, Japan and Irvington, Ala. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'YHLAX15' as a new and distinct cultivar of *Hydrangea* plant:

1. Light pink-colored inflorescences under alkaline growing conditions;
2. Light violet-blue colored inflorescences under acidic growing conditions;
3. Medium green-colored foliage; and
4. Moderately vigorous, upright growth habit.

Plants of the new cultivar differ from plants of the female parent primarily in having florets with a wavy sepal margin. Plants of the new cultivar differ from plants of the male parent primarily in inflorescence type and color and in having florets with a wavy sepal margin.

Of the many commercially available *Hydrangea* cultivars, the most similar in comparison to the new cultivar is 'Nikko Blue', not patented. However, in comparison, plants of the new cultivar differ from plants of 'Nikko Blue' in at least the following characteristics:

1. Plants of the new cultivar have an inflorescence color different from plants of 'Nikko Blue'; and
2. Plants of the new cultivar have a floret sepal margin different from plants of 'Nikko Blue'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'YHLAX15'. The plants were approximately one-year old and were grown in one-gallon containers for approximately 7 months in a poly-covered greenhouse in West Chicago, Ill. Plants were given one pinch at transplant.

DETAILED BOTANICAL DESCRIPTION

Figure 1:
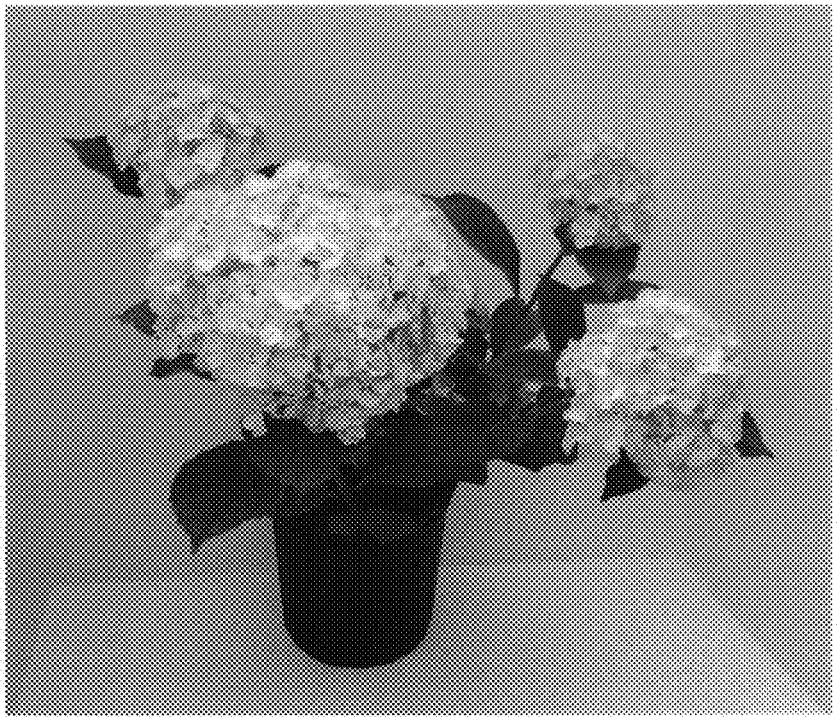
FIG. 1 illustrates a side view of the overall growth and flowering habit of 'YHLAX15'.
Figure 2:
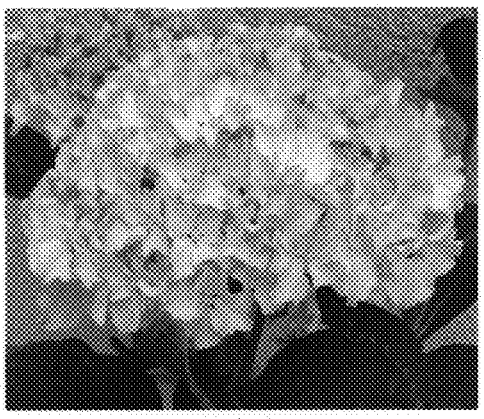
FIG. 2 illustrates an inflorescence with first-open florets of 'YHLAX15'.
Figure 3:
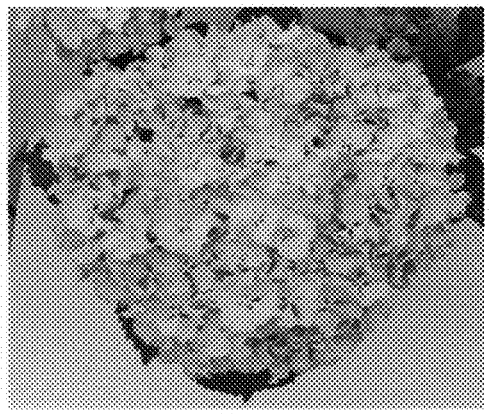
FIG. 3 illustrates an inflorescence with fully-open florets of 'YHLAX15'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2016 under natural light conditions in West Chicago, Ill. Color values for acidic growing conditions were obtained from plants grown in Narita, Japan.

The following descriptions and measurements describe approximately one-year old plants produced from softwood cuttings from stock plants and grown under conditions comparable to those used in commercial practice. The plants were grown in one-gallon containers for approximately 7 months in a poly-covered greenhouse in West Chicago, Ill. Plants were given one pinch at transplant. During winter months supplemental heat was provided to maintain temperatures above a minimum of 38° F. (3.3° C.). No supplemental lighting was provided. Measurements and numerical values represent averages of typical plants.

Botanical classification:

*Hydrangea macrophylla* cultivar YHLAX15.

Parentage:

*Female parent.*—Proprietary *Hydrangea macrophylla* breeding selection coded TKH2000, not patented.

*Male parent.*—'Kiyosumi sawa', not patented.

Propagation:

*Type cutting.*—Softwood cuttings.

*Time to initiate roots during the summer.*—Approximately 16 days.

*Time to produce a rooted cutting during the summer.*—Approximately 28 days.

*Time to initiate roots during the winter.*—Approximately 18 days.

*Time to produce a rooted cutting during the winter.*—Approximately 31 days.

*Root description.*—White to grey, medium thickness, fibrous.

*Rooting habit.*—Moderate branching and density.

Plant description:

*Commercial crop time.*—Approximately 30 to 34 weeks of cultivation from a rooted cutting followed by 9 to 11 weeks of forcing to finish in a 13.0 cm pot.

*Growth habit and general appearance.*—Deciduous shrub, mophead-type *Hydrangea*; moderately vigorous, upright growth habit.

*Hardiness.*—USDA Zone 5 (−20° F. to −15° F.).

*Heat tolerance.*—Regularly tolerates temperatures as high as 38° C. in the summer.

*Size.*—Height from soil level to top of plant plane: Approximately 41.0 cm. Width: Approximately 48.0 cm.

*Branching habit.*—Freely branching. Pinching enhances branching. Quantity of lateral branches per plant: Approximately 5.

*Branch.*—Shape: Rounded. Strength: Strong. Length to base of inflorescence: Approximately 35.0 cm. Diameter: Approximately 5.0 mm. Length of central internode: Approximately 7.0 cm. Texture of young stem: Glabrous. Texture of mature stem: Glabrous, becoming woody with age. Color of young stem: 145A. Color of mature stem: 146C to 146D, becoming 199A with age.

*Lenticels.*—Quantity per internode: Approximately 15. Shape: Round to elliptic. Size: Approximately 1.0 mm to 4.0 mm. Color: N77A.

Foliage description:

*General description.*—Quantity of leaves per lateral branch: Approximately 8. Fragrance: None detected. Form: Simple. Arrangement: Opposite.

*Leaves.*—Aspect: Flat. Shape: Elliptic. Margin: Serrated. Apex: Acuminate. Base: Broadly attenuate. Venation pattern: Pinnate. Length of mature leaf: Approximately 12.2 cm. Width of mature leaf: Approximately 8.3 cm. Texture of upper and lower surfaces: Coriaceous, glabrous. Color of upper surface of young foliage: 137A blended with 144A, venation of 146D. Color of lower surface of young foliage: Closest to 146B with venation of 146D. Color of upper surface of mature foliage: 137A blended with 144A, venation of 146D and midvein of 145C. Color of lower surface of mature foliage: Closest to 146B with venation of 146D and midvein of 145C.

*Petiole.*—Length: Approximately 3.0 cm. Diameter: Approximately 5.0 mm. Texture: Glabrous. Color: 145C.

Flowering description:

*Flowering habit.*—Seasonal, May through August.

*Lastingness of individual inflorescence on the plant.*—Approximately 4 weeks.

Inflorescence description:

*General description.*—Type: Terminal globular, mophead, compound corymb of fertile florets and sterile, sepalous florets borne on the same corymb, persistent. Sterile florets occasionally have visible reproductive parts, but lack an ovary. Quantity per plant: Approximately 4. Fragrance: None detected. Aspect: Face upward and outward. Height: Approximately 9.0 cm. Width: Approximately 14.0 cm to 19.0 cm. Quantity of fertile florets per inflorescence: Approximately 90. Quantity of sterile florets per inflorescence: Approximately 250 to 300.

*Peduncle.*—Strength: Strong. Shape: Rounded. Length: Approximately 4.0 cm. Diameter: Approximately 3.0 mm. Texture: Densely pubescent with appressed hairs. Color: 145A.

Floret description:

*General description.*—Type: Single, sterile and fertile.

*Sterile florets, bud just before opening.*—Shape: Globular. Diameter: Approximately 2.0 mm. Color: 145A.

*Sterile florets.*—Depth: Approximately 5.0 mm to 1.0 cm. Diameter: Approximately 3.1 cm. Corolla: 4 to 5 petals, often closed forming a central eye. Shape: Rotate, cruciform if 4 petals. Diameter: Approximately 7.0 mm. Calyx: 4 to 5 sepals. Shape: Rotate, cruciform if 4 sepals. Diameter: Approximately 3.1 cm.

*Petals, sterile florets.*—Shape: Ovate, cupped when open, otherwise petals form a center eye of up to 2.0 mm in diameter and 73D in color. Margin: Entire. Apex: Acute. Base: Truncate. Length: Approximately 3.5 mm. Width: Approximately 2.0 mm. Texture of upper and lower surfaces: Glabrous. Color of upper and lower surfaces: NN155D with a faint overlay of 73C.

*Sepals, sterile florets.*—Shape: Broadly ovate. Margin: Crenate, wavy. Apex: Broadly acute. Base: Broadly attenuate. Length: Approximately 1.5 cm. Width: Approximately 1.6 cm. Texture of upper surface: Glabrous. Texture of lower surface: Sparsely pubescent. Color of upper surface when first open: 145B while opening, transitioning to NN155B with margins of 73B; under acidic growing conditions transitioning to NN155D with an overlay of closest to 97A and margin of N78A. Color of lower surface when first open: 145C while opening, transitioning to NN155C with margins of 73C; under acidic growing conditions transitioning to NN155D with an overlay of closest to 97B. Color of upper surface when fully open: NN155D with an overlay of 73A, color most intense at apex; under acidic growing conditions NN155D with an overlay of closest to 97A. Color of lower surface when fully open: NN155D with an overlay of 73B, color most intense at apex; under acidic growing conditions NN155D with an overlay of closest to 97B.

*Pedicel, sterile florets.*—Strength: Strong. Aspect: Approximately 45° from peduncle axis. Length: Approximately 2.0 cm. Diameter: Approximately 1.0 mm. Texture: Sparsely pubescent with appressed hairs. Color: 73C.

*Fertile florets, bud just before opening.*—Shape: Globular. Diameter: Approximately 3.0 mm. Color: NN155C with an overlay of 73B.

*Fertile florets.*—Depth: Approximately 4.0 mm. Diameter: Approximately 7.0 mm. Corolla: 4 to 5 petals. Shape: Rotate, cruciform if 4 petals. Diameter: Approximately 7.0 mm. Calyx: 4 to 5 sepals. Shape: Rotate, cruciform if 4 sepals. Diameter: Approximately 5.0 mm.

*Petals, fertile florets.*—Shape: Ovate, cupped. Margin: Entire. Apex: Acute. Base: Truncate. Length: Approximately 3.5 mm. Width: Approximately 2.0 mm. Texture of upper and lower surfaces: Glabrous. Color of upper and lower surfaces: NN155D with a faint overlay of 73C.

*Sepals, fertile florets.*—Shape: Ovate. Margin: Entire. Apex: Acute. Base: Truncate. Length: Approximately 2.0 mm. Width: Approximately 1.0 mm. Texture of upper surface: Glabrous. Texture of lower surface: Moderately pubescent. Color of upper and lower surfaces: 145B slightly tinted with 73B.

*Pedicel, fertile florets.*—Strength: Strong. Aspect: Erect. Length: Approximately 3.0 mm. Diameter: Approximately 1.0 mm. Texture: Densely pubescent with appressed hairs. Color: 145B slightly tinted with 73B.

*Reproductive organs.*—Observed in fertile florets and occasionally in the center of sterile florets, sterile florets lack an ovary. Androecium: Stamen quantity: Approximately 10 per floret. Stamen length: Approximately 3.0 mm to 4.0 mm. Filament color: NN155D. Anther shape: Kidney-shaped, basally attached. Anther length: Approximately 1.0 mm. Anther color: NN155A. Pollen amount: Moderate. Pollen color: NN155D. Gynoecium: Pistil quantity: 1 per floret. Pistil length: Approximately 4.0 mm. Stigma shape: Round. Stigma color: NN155D. Style length: Approximately 2.0 mm, three to four-lobed. Style color: NN155D. Ovary length: Approximately 2.0 mm. Ovary texture: Sparsely pubescent with appressed hairs. Ovary color: 145B slightly tinted with 73B.

Seed and fruit production: Neither seed nor fruit production has been observed.

Disease and pest resistance: Resistance to pathogens and pests common to *Hydrangea* has not been observed.

What is claimed is:

1. A new and distinct cultivar of *Hydrangea* plant named 'YHLAX15', substantially as herein illustrated and described.

* * * * *